US005744094A

United States Patent [19]

[11] Patent Number: 5,744,094

[45] Date of Patent: Apr. 28, 1998

Castberg et al.

[54] TREATMENT OF MATERIAL

[75] Inventors: Helge Bakketun Castberg, Kolbotn, Norway; Karin Bergmann, Willingham, United Kingdom; Peter John Hyde, Cowlinge, United Kingdom; Karen Margaret Montgomery Ness, Glasgow, United Kingdom; Christopher John Stanley, St. Ives, United Kingdom

[73] Assignee: Elopak Systems AG, Glattbrugg, Switzerland

[21] Appl. No.: 122,599

[22] PCT Filed: Apr. 13, 1992

[86] PCT No.: PCT/GB92/00671

§ 371 Date: Feb. 24, 1994

§ 102(e) Date: Feb. 24, 1994

[87] PCT Pub. No.: WO92/18170

PCT Pub. Date: Oct. 29, 1992

[30] Foreign Application Priority Data

Apr. 12, 1991 [GB] United Kingdom .................. 9107751

[51] Int. Cl.[6] ................................ A61L 2/10; A61L 2/16

[52] U.S. Cl. ................................ 422/24; 422/22; 422/28; 250/455.11; 250/492.1; 250/495.1; 426/241

[58] Field of Search ................................ 422/22, 24, 28; 250/455.11, 495.1, 492.1; 426/237, 241, 248

[56] References Cited

U.S. PATENT DOCUMENTS

| | | | |
|---|---|---|---|
| 3,817,703 | 6/1974 | Atwood | 21/2 |
| 3,941,670 | 3/1976 | Pratt, Jr. | 204/158 R |
| 4,035,981 | 7/1977 | Braun et al. | 53/426 |
| 4,115,280 | 9/1978 | Pratt, Jr. | 422/186.1 |
| 4,175,140 | 11/1979 | Bachmann et al. | 422/24 X |
| 4,289,728 | 9/1981 | Peel et al. | 422/24 |
| 4,366,125 | 12/1982 | Kodera et al. | 422/24 X |
| 4,375,145 | 3/1983 | Mosse et al. | 53/425 |
| 4,661,264 | 4/1987 | Goudy, Jr. | 422/24 X |
| 4,797,255 | 1/1989 | Hatanaka et al. | 422/28 |
| 4,806,768 | 2/1989 | Keutenedjian | 422/24 X |
| 4,964,698 | 10/1990 | Rowlette | 350/320 |
| 5,068,514 | 11/1991 | Lunney | 219/121.69 |
| 5,099,557 | 3/1992 | Engelsberg | 250/492.1 X |
| 5,114,670 | 5/1992 | Duffey | 422/24 |
| 5,439,642 | 8/1995 | Hagmann et al. | 422/22 |

FOREIGN PATENT DOCUMENTS

| | | | |
|---|---|---|---|
| 0152072 | 8/1985 | European Pat. Off. . | |
| 0201650 | 11/1986 | European Pat. Off. | C02F 1/32 |
| 2914075 | 11/1980 | Germany | A61L 2/10 |
| 60-28235 | 2/1985 | Japan . | |
| 80/0145 | 7/1980 | WIPO | A61L 2/18 |
| 88/03369 | 5/1988 | WIPO | A23L 3/26 |

*Primary Examiner*—Robert J. Warden
*Assistant Examiner*—E. Leigh Dawson
*Attorney, Agent, or Firm*—Reising, Ethington, Barnard & Perry

[57] ABSTRACT

A sterilizing method includes subjecting material, for example packaging board, to laser UV alone, or substantially simultaneously with laser IR and/or hydrogen peroxide to obtain a synergistic effect between the UV and IR and/or hydrogen peroxide, to render micro-organisms present at said material non-viable.

43 Claims, 2 Drawing Sheets

TREATMENT OF MATERIAL

This invention relates to the treatment of material, in particular the subjection of material to laser UV.

BACKGROUND OF THE INVENTION

It is known to sterilise packaging material, for example the inside surfaces of cartons, in a variety of ways, used together or separately. One is to use heat, for example in the form of hot air or steam, at a temperature above 100° C. for several seconds. Another treatment is to use UV radiation of a bactericidal wavelength (for example 254 mm) giving an average power density at the treatment surface of the order of mW/$cm^2$, for example 8 mW/$cm^2$, for many seconds. A further treatment is to employ a relatively highly concentrated $H_2O_2$ solution for several seconds. The combining of two or more of the treatments is conventional and enables certain parameters of the treatments, for example the temperature, the treatment time, and/or the $H_2O_2$ concentration to be reduced. For example, WO-A-80/01457 discloses a sterilization method applicable to liquids, e.g. waste water and cannery cooling water, but particularly for the sterilization of surfaces, for example surfaces of walls and furniture in hospitals and the surfaces of food containers. The latter surfaces are treated with a concentration of $H_2O_2$ no greater than 10% by weight, for example by passing the container or material from which the container will be fabricated through a tank containing the $H_2O_2$ solution or by spraying the surfaces of the container or material with the solution. Irradiation is carried out by an UV-lamp so disposed that containers or materials which have emerged from the tank or spray are subjected to UV of wholly or predominantly below 325 nm., such that micro-organisms are rendered non-viable by synergism between the UV and the $H_2O_2$.

The use of ultraviolet radiation as a physical agent for the reduction of micro-organisms is well-established. Cellular DNA absorbs the energy of radiation between 250 and 260 nm which leads to the formation of chemical bonds between adjacent thymine nucleotide bases. This change distorts the DNA strands, interfering with replication and transcription and thus expression of the genes. Fatality is inevitable if essential genes are blocked or DNA replication is hindered. The number of vegetative cells killed with UV radiation depends on exposure and dose in mW/$cm^2$ and mJ/$cm^2$, respectively, and UV is often ineffective in the killing of bacterial endospores, particularly because UV has poor penetrating power. The combined use of UV radiation, hydrogen peroxide (peroxide radical reacts with most chemical bonds) and heat, achieves sterilisation, but at a high price in terms of time and cost (for example at least 10 seconds treatment time per carton) to the packager. Also the use of a chemical, for example $H_2O_2$, for the treatment of food packaging can be an ethical consideration and thus classed as less desirable. It is therefore very attractive to search for an alternative sterilisation system.

WO-A-88/03369 discloses a system for sterilizing such things as air, water, food and food packaging by means of intermittent, very intense, very short duration pulses of light in the visible and near visible frequencies, such light being produced by flashlamps, for example. The components of each pulse cover a broad spectral range and may include far and near UV for deactivation of micro-organisms through photochemical effects. Such UV-rich pulses have at least 15% and preferably at least about 30% of their energy at wavelengths shorter than 300 nm. Such UV-rich pulses may typically have relatively low total energy density, such as in the range of from about 0.01 to 15 J/cm.$^2$ and typically from about 0.1 to 3 J/cm.$^2$. However, for treating food product surfaces, it may be desirable to filter out portions of the spectrum, so that at least about 90% of their energy is distributed between 300 and 2500 nm. In such methods in which the UV-component of the pulsed light flashes is suppressed or substantially eliminated, the intensity of the pulsed light should be sufficient to heat a superficial layer of the foodstuff or packaging material having a thickness of less than 10 microns, through at least about 50° C. to a temperature of at least about 75° C. and preferably at least about 100° C.

EP-A-0201650 discloses a system for laser disinfection of fluids, in which a laser beam which radiates light in the UV range is directed into a stream of the fluid to be treated. The system is particularly applicable to the treatment of water and employs a gas pulsed laser the pulsing rate and therefore the average UV light intensity of which can be adjusted. The UV beam fills the cross-section of the water stream. The rate may vary from slow to so rapid as to be an essentially continuous beam and is adjusted for changes in the flow rate of the water stream passing through the laser beam and can also be adjusted for changes in the turbidity of the water. Alternatively, the stream flow rate can be varied and the UV beam intensity kept constant. One or more surfaces of the conduit guiding the stream can be made relatively highly reflective of UV to confine the spreading of the beam due to suspended particles in the water and to decrease the beam cross-sectional area to compensate for alteration of the beam so as to maintain a nearly uniform intensity along the length of the region in which the beam and the stream interact. The angle of penetration of the beam into the stream may be adjusted in response to changes in the turbidity of the water. Moreover, the geometry of the beam, in particular its length, may be altered in response to changes in water characteristics, such as organic content. A fluorine krypton excimer laser producing a wavelength of 249 nm. is preferred.

U.S. Pat. No. 3,817,703 relates to a method for destroying living matter suspended in light transmissive material. It discloses the possibility of sterilizing simultaneously containers and materials stored therein by directing a laser beam at the container so that the beam contacts all interior surfaces of the container during the sterilization process and thereby also subjects all of the material in the container to the light rays. Living matter suspended in the material or clinging to the interior container walls is thereby destroyed. One or more oscillatable mirrors are employed to cause one or more laser beams to scan the container.

U.S. Pat. No. 3,941,670 discloses use of an IR-laser the target of which may be scanned by the laser beam by oscillation of a mirror. The light alters the biological activity of macromolecular species by exciting vibrational and rotational states of the irradiated species. Various targets may be sterilized, for example air or other fluids, plastics or metals, such as a strip or ribbon of aluminium foil.

DE-A-2914075 discloses a system for sterilizing the inside surfaces of pre-formed folded cartons. UV sources, for example vertical, mercury-vapour sources are downwardly insertable into respective cartons at differing positions relative to the side walls of the cartons, so that, as each carton receives the UV sources in turn, UV radiation of sufficient intensity reaches the otherwise shadowed angular areas created by bottom and side seams of the carton. An embodiment provides for the UV sterilization to be combined with heat sterilization, so that heat-sensitive yeasts and moulds can be eliminated. Such heat sterilization can be carried out by steam or by irradiation, namely infra-red radiation sources, which are similarly inserted into the carton, before or after the UV sources.

SUMMARY OF THE INVENTION

According to a first aspect of the present invention, there is provided a method of sterilizing a solid surface, comprising irradiating said surface with UV of a wavelength which is bactericidal, characterized in that said UV is laser UV.

According to a second aspect of the present invention, there is provided a method of subjecting a surface of a three-dimensional object to laser radiation, characteried in that the direction and intensity of the radiation are so controlled as to produce a relatively even radiation intensity over said surface.

According to a third aspect of the present invention, there is provided a method of sterilising a material comprising irradiating the same with IR and with UV to produce at said material a bactericidal effect, characterized in that the irradiation with IR and UV is carried out substantially simultaneously.

According to a fourth aspect of the present invention, there is provided a method of sterilizing a material, comprising irradiating the same with IR and UV to produce at said material a bactericidal effect, characterized in that said UV is laser UV.

According to a fifth aspect of the present invention, there is provided a method of sterilising a material, comprising irradiating the same with laser UV and exposing the same to hydrogen peroxide to produce at said material a bactericidal effect, characterized in that said UV is laser UV.

It is of course well known that thermoplastics surfaces of packaging material, for example the surfaces of thin polymer layers, are particularly sensitive to heat. However, we have found that, using laser UV, it is possible to irradiate those surfaces with an average power density greater than 1 $W/cm^2$, advantageously in the range between 4 $W/cm^2$ and 10 $W/cm^2$, without deleteriously affecting the thermoplastics surface i.e. melting the surface. The energy density is advantageously greater than 50 $mJ/sec./cm^2$, applied for less than 10 seconds.

It is also feasible to employ UV, whether laser UV or not, to sterilise a material and at the same time to use IR, whether laser IR or not, to heat that material, the heating of the material serving the purpose of promoting more rapid sterilisation and/or the purpose of rendering the material tacky or molten for sealing and/or the purpose of suppressing foam formed in the packaging contents during filling. The application of IR and UV in that manner is either simultaneous or overlapping in time.

In order to obtain a relatively high power density, the UV and/or IR may be focussed to a spot which is caused to perform a scanning displacement, for example by the use of mirrors. The IR and/or UV may be diffracted through a computer-generated hologram so as to obtain a relatively even power density over a three-dimensional surface to be treated. Although an important aspect of the invention is the use of laser UV alone to sterilise a solid continuous surface, $H_2O_2$ may be used with the laser UV (and laser IR) to produce the sterilisation. We have found that the use of laser UV combined with $H_2O_2$ has a synergistic effect from a bactericidal point of view.

We have also found that, with increasing levels of density of micro-organisms, there is a relatively sudden drop of viability of the sterilising method, giving a so-called "cliff" effect.

In our opinion pulsed UV is particularly advantageous, especially in being more effective, for sterilising a solid surface, compared with continuous UV.

The UV wavelength employed is preferably in the range from 150 to 320 nm, advantageously 240 to 280 nm, for example about 250 nm. The IR wavelength employed is preferably in the range between about 1000 and about 10,000 nm.

The use of a laser to provide the UV, as opposed to a germicidal lamp emitting UV, has been found to give the following advantages:

(1) relatively high absolute energy densities (2) a low divergence, highly directional output beam, which makes it especially suitable for the treatment of specific areas within cartons where contamination might be severe, e.g. carton corners and folds.

BRIEF DESCRIPTION OF THE DRAWINGS

In order that the invention may be clearly understood and readily carried into effect, reference will now be made to the following drawings and examples.

DESCRIPTION OF THE PREFERRED EMBODIMENTS

Example I

Figure 1:
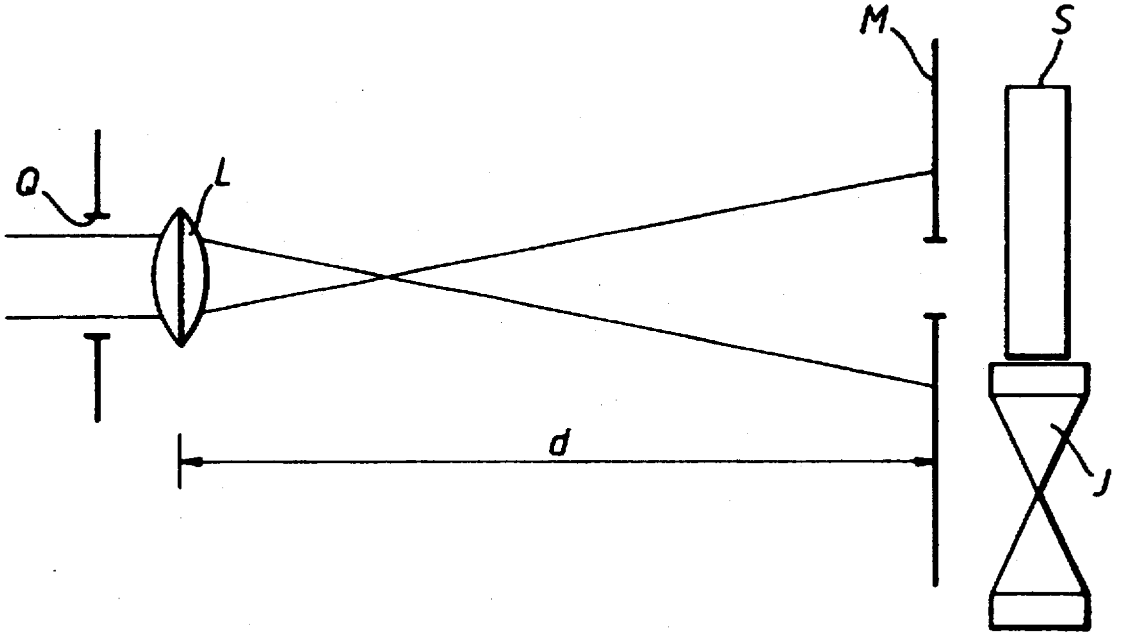
FIG. 1 shows diagrammatically apparatus used in the exposure of test strips to laser UV.

The target organism for the investigation of the laser treatment was chosen to be the endospore-forming bacteria: *Bacillus subtilis var. globigii*. This bacteria is classified as Gram positive, aerobic, rod-shaped, motile and is non-pathogenic. It is ubiquitous in its habitat and can be found in soil, faeces, hay dust, milk and water. The formation of spores enables bacteria to survive in a latent state (dormant and viable) for a long time, and makes it particularly important that sterilisation systems are capable of killing these endospores. Since spores are resistant to temperatures above 100° C. and other destructive agents (chemicals) they make useful indicators for the effectiveness of sterilisation and are regularly employed to monitor chemical sterilisation and heat treatments. Standard microbiological tests and microscopic investigations are used in the testing of samples for the evaluation of a new sterilisation procedure. The identification of spores under the microscope is aided by their high refractivity and reduced susceptibility to staining and by their specific reaction to certain dyes.

Blank carton material (a paperboard layer laminated with polyethylene layers, with and without an aluminium foil barrier layer) and *Bacillus subtilis var. globigii* spore suspension obtained from Elopak A/S in Norway were used throughout the study. A second bacterial culture (NCIMP 8649) was used as control alongside the provided culture, serving as an independent confirmation of the species. The methodical procedure divided into three main stages, namely the coating of bacteria onto the test strips and all associated pre-coating procedures, the exposure of the strips to laser UV and the subsequent analysis of these strips.

A test system was devised for the coating of the culture onto the carton material in the form of test strips with emphasis on sterility of the strips prior to coating and specific placement of the bacteria onto the sterile surface, so that sterility of the strips was ensured.

The carton material was cut with scalpel blades to give test pieces of 6 $cm^2$ and 2 $cm^2$. These test strips were [exposed to several different sterilisation treatments:

Hydrogen peroxide 35%, 1 ml/test strip, for 2 min

Hydrogen peroxide 2%, 1 ml/test strip, for 2 sec and for 2 min

Steam sterilized in an autoclave at 121° C. for 20 min.

All strips were allowed to dry well before the bacterial culture was applied and a number of sterile strips were set aside to act as controls.

Sterilised strips were kept in autoclave bags at room temperature up to 4 days prior to use. Coated test strips were stored in petri-dishes at 4° C. for up to 4 days.

*Bacillus subtilis var. globigii* spore suspension was subcultured into nutrient broth (beef extract, peptone, water, pH 6.8), grown at 37° C., and investigated after 24 hours. Standard 'pour-plate' methods were employed to isolate colonies and for making viable counts. Nutrient broth and sterile distilled water were used depending on the 'pour-plate' method used. Nutrient agar (beef extract, peptone, agar pH 6.8) served as the solid medium for growth of the organism. There was visual observation and counting of the colonies after 36 hours of incubation at 37° C. Pure cultures were used for smear preparations and subsequent differential staining procedures. The stains used were Gram stain and Ziehl-Nielsen's endospore stain and the stained slides analysed with a light microscope (10×100).

100 µl aliquots from a serial dilution of the starting culture giving $10^3$ and $10^6$ cfu/ml in distilled water were aseptically dispensed onto a sterile carton test strip, spread out and left to dry for several hours. The test strip was kept covered in a sterile petri-dish during the drying time at room temperature and afterwards for storage at 4° C. Great care was taken to keep the petri-dish upright at all times to avoid accidental contamination of the non-laminated surface.

One test strip per serial dilution and two sterile samples were placed separately into 10 ml of nutrient broth and growth was investigated after 36 hours at 37° C. Turbidity was visually assessed and followed by plating of 100 µl of the growth medium onto nutrient agar plates for another incubation period of 36 hrs at 37° C. and slide observations were then made as described above.

The laser (the aperture of which is indicated at Q in the diagrammatic FIG. 1 of the accompanying drawings) used was Questek 2000 Series excimer laser operating on the Krypton Fluoride (KrF) transition which produces radiation in the ultra-violet at 248 nm. The excimer laser is pulsed, producing 10–20 ns pulses at repetition rates up to a few hundred Hertz.

The following operating parameters were used:

Pulse energy: 200 mJ

Repetition rate: 100 Hz

The laser emits a beam which is approximately 3×2 cm (horizontal×vertical).

The optical system used is shown in the Figure. The energy density at the sample S was varied by changing a fused silica lens L, and/or the distance d from the lens to a mask M, and thus from the lens to the sample.

Initially, a 25 cm focal length cylindrical lens was used to expand the beam in the horizontal dimension, producing an approximately 3×3 cm irradiation area at the mask M. The resulting energy density/shot on the sample was 40 mJ/$cm^2$, giving an average power density of 4 W/$cm^2$ at 100 Hz.

To produce a higher power density at the sample, the distance to the sample was reduced and the sample size also reduced accordingly, from 3×3 cm to 1×1 cm. The energy/shot and average power densities with this configuration were 130 mJ/$cm^2$ and 13 W/$cm^2$ respectively.

To allow lower irradiation densities, the cylindrical lens was replaced by a spherical lens, focal length 20 cm. The resulting beam area at the sample overfilled the mask aperture substantially, resulting in energy/shot and average power densities at the sample of 10 mJ/$cm^2$ and 1 W/$cm^2$, respectively.

In all cases, the energy density was measured at the plane of the mask aperture. The sample block was a few centimeters behind this plane. However the difference in exposure introduced by this was small as the offset was small compared with the distance d, which was typically in the range 40–70 cm.

Various irradiation times were used, depending on the energy and power densities tested:

10 mJ/shot/$cm^2$: 1 s and 6 s 40 mJ/shot/$cm^2$: 1 s and 6 s 130 mJ/shot/$cm^2$: 15 s The prepared test strips were mounted, using sterilised pins, on a balsa wood block covered with aluminium foil. Both the block and the foil were steam sterilised for 20 min at 121° C. before use. Depending on the size of the test strips, twelve to sixteen samples were treated on a single block, the block being mounted on a labjack J to provide 'scanning'. The mounting of the samples on the block was under hygienic conditions, using sterilised forceps for the affixing of the strips.

Experiments with $H_2O_2$ were set up as follows:

a) addition of 100 µl 2% $H_2O_2$ to the test strip (one for each test dilution), spread over the carton surface, heat dried, then exposed to the laser beam b) as a) but not heat dried before the laser beam exposure—test strips were sandwiched in between sterile silica glass plates—laser treated and then heat dried The heat applied was approximately 100° C. through contact of the bottom silica plate to a laboratory heat plate. The top silica plate was removed for the drying process.

All laser beam exposed samples, including the control samples, were immediately placed into separate universal containers with 10 ml of sterile nutrient broth and incubated for 36 hours at 37° C. Sterility was investigated via assessment of turbidity of the solution after the incubation period and followed by subculturing onto nutrient agar plates and a second incubation of 36 hours at 37° C. and growth was microscoped for presence of indicator strain.

Sterilisation treatments of the test strips showed the autoclave method as the most reliable and successful procedure.

The drying method of the bacterial culture onto the test strips was successful with viable colony growth of samples up to 4 days old (test strips older than 4 days were not tested). The serial dilution and subsequent 'pour-plate' method established the bacterial culture as containing $2\times10^7$ cfu (colony forming units) per ml. (5 agar plates per dilution series were used to establish an average number of colonies). The sterile strips without bacterial addition, used as controls throughout the study and indicators for the successful application of aseptic techniques, were found to remain sterile in most experiments. In two cases where cards had been in contact with a non-sterile surface the test strips were cultured and a Gram negative organism identified.

In all of the experiments the use of Gram stain and endospore staining of the *Bacillus subtilis var. globigii* bacteria clearly identified the organism as a *Bacillus subtilis* species.

The classification of results into sterile and non-sterile was without ambiguity, as was the differentiation of the test organism from other potential contaminants.

SUMMARY OF RESULTS AFTER LASER EXPOSURE

| Power Density ($W/cm^2$) | Laser Treatment Conditions Exposure Time | 2% $H_2O_2$ used? | Test strip size (cm × cm) | Replicates number | Sterile rate after 36 hours and initial cell density |
|---|---|---|---|---|---|
| 13 | 15 | No | 1 × 1 | 2 each | 1 at $10^6$ |
| 4 | 1 | Yes | 1 × 1 | 5 each | 1 at $10^6$ |
| 4 | 6 | Yes | 1 × 1 | 5 each | 1 at $10^3$<br>3 at $10^6$ |
| 4 | 1<br>6 | No | 1 × 1 | 2 each | 1 at $10^6$, 1s<br>2 at $10^6$, 6s |
| 4 | 1<br>6 | No | 2.5 × 2.5 | 2 each | none |
| 4 | 1<br>6 | Yes | 2.5 × 2.5 | 2 each | 2 at $10^3$, 6s<br>1 at $10^6$, 6s<br>1 at $10^3$, 1s |
| 4 | 1<br>6 | Yes<br>(silica glass) | 2.5 × 2.5 | 2 each | 2 at $10^3$, 1s<br>2 at $10^6$, 6s<br>1* at $10^6$, 1s<br>2 at $10^3$, 6s |
| 13 | 5 | Yes<br>(silica glass) | 1 × 1 | 4 each | 4 at $10^6$<br>3* at $10^3$ |
| 1 | 1<br>6 | No | 3 × 3 | 5 each | none |

*hand contamination on one sample

Some encouraging results were obtained, thereby demonstrating that the effective killing of micro-organisms can be achieved with the use of laser UV. With a 4 $W/cm^2$ average power density for 6 seconds exposure time, the killing efficiency (defined as the number of sterile test strips/total number of test strips illuminated×100) was about 30%. The inclusion of hydrogen peroxide on the test strip improved this to close to 100%. It should be noted that the excellent result with $H_2O_2$ was achieved with an illumination time of only 1 second.

Example II

The results of Example I were indicative of a successful killing effect of laser UV on micro-organisms such as *Bacillus subtilis*. Laser illumination periods from 1 second to 6 seconds, at 40 mJ/shot/$cm^2$ (4 $Wcm^2$) were shown to kill $10^3$ to $10^6$ bacterial cells in several samples.

The quantitative assessment of how many organisms are killed by a specific laser treatment was further investigated in this Example. A high number of samples was tested to monitor the killing efficiency of different laser illumination procedures with particular emphasis on varying the power density and repetition rates. The sensitivity of the laser light sterilisation procedure was measured by observation of bacterial survival rates after different treatments.

Several other experimental questions were investigated throughout the study. These were as follows:

How does the background foil, on which the strips are placed, affect the heat generated and how does this extra heat, if present, affect the killing potential of the laser?

Does the wood used for mounting of the strips release a substance into the strips that might aid the destruction of the bacteria? Is this substance, if present, activated by autoclaving and taken up by the strip?

Is the strips itself releasing substances that might affect the bacterial kill rate? Is the heat generated by the laser necessary for the actual killing of the bacteria?

How does a reduction in power density ($W/cm^2$) and/or a reduction in repetition rates (Hz) affect the killing efficiency of laser UV illumination?

Blank carton material (Al-foil laminate) and "STUDLAND" mounting board card (non-laminated) were used in the study. A *Bacillus subtilis var. globigii* spore suspension was used to prepare a serial dilution in distilled water. This dilution series was aliquotted onto the test strips, allowed to dry and exposed to laser UV.

The procedures divided into three main stages, namely the coating of the bacteria onto the sterilised test strips, the exposure of the strips to laser UV and the subsequent analysis of these strips.

The carton material and card was cut with scalpel blades to give test strips of 1.3 cm×1.3 cm. 18 test strips were used per block of balsa wood (the wood was covered with Al-foil or left uncovered). The layout of the strips on the wood was three rows in total per block with six strips per row.

All strips were kept in place with autoclave tape so that a 1 $cm^2$ carton area per strip remained exposed. Each block was placed into a separate autoclave bag and autoclaved at 121° C. for 20 minutes.

50 μl of each prepared dilution ($10^{-1}$, $10^{-2}$, $10^{-3}$, $10^{-4}$ of a starting culture *Bacillus subtilis var. globigii* was aseptically aliquotted onto the strips and left to dry under laminar air flow conditions for several hours. Two strips per block were used as controls, i.e. no exposure to laser UV and one strip per block was used as a blank, i.e. no bacterial dilution was added. Each block of balsa wood with the strips was then returned to the sterile autoclave bag and sealed until the laser UV treatment.

To provide a baseline from which bacterial kill could be estimated, the number of colony forming units deposited on strips from the various dilutions was assessed using a detergent recovery method as follows:

The prepared strips with the appropriate bacterial dilution were immersed in 0.1% Tween 20 (sterile distilled water dilution).

The Tween 20 recovery efficiency of the inoculated strips was compared to a sterile water recovery so that a proof of principle of the method could be established.

Other method variations to see if an effect on bacterial numbers was present, included comparisons between strips mounted on balsa wood or left unmounted in sterile petridishes before recovery.

The laser used was as in Example I, but with an increased pulse energy of 250 mJ. The only variations introduced were the repetition rate (Hz), illumination times and energy density used. The variations tested were as set out in the "Laser Parameters" column of the following Table.

A 25 cm cylinder lens was again used to reduce the vertical dimension of the beam to achieve an energy density of 40 mJ/shot/cm$^2$. A 35 cm focal lens was used to expand the beam so that the lower energy density of 6 mJ/shot/cm$^2$ could be achieved.

Up to 18 strips were treated on a single block, the block being mounted on the labjack J to provide scanning. the scanning procedure was under hygienic conditions and the blocks placed into sterile autoclave bags after the treatment. The bags were sealed and stored at room temperature until subsequent analytical procedures were initiated. On most blocks there were three strips that did not receive the laser UV illumination (two of these samples were used as controls and one strip—without bacteria—was used as a blank control).

All mounted strips were aseptically removed from the blocks, added to separate bottles containing 5 ml of diluent and vortexed for a minimum of 30 seconds. 100 µl of each sample was pipetted onto separate nutrient agar plates, streaked out and incubated at 37° C. for a minimum of 24 hours.

The plates were visually inspected for colony growth and colony numbers were counted.

Nutrient agar plating procedure of the serial dilution resulted in a repeatable number of colonies per bacterial concentration and allowed calculation of the recovery factor.

It was found that the best method for recovering bacteria from the strips was the use of a 1 minute vortex in the diluent. Recovery ranged from 50% to 90% of the bacteria on the strip. The serial dilution experiment showed that there were $1.5\times10^7$ cfu/ml. in the starting culture.

The two types of material tested did not show any attributable difference in the recovery rate obtained. The experiment with test strips on the balsa wood in comparison to the strips that were left in petri-dishes also did not reveal any difference in results, thus excluding any potential chemical effect through the backing support itself.

The results from experiments before the laser exposure such as investigations into the potential bactericidal substances within the material or the wood were further studied with test strips subjected to laser UV illumination, but no effects were found. Any potential heating effect on the bacterial kill rate was conclusively negated when the heat intensity of the laser UV illumination was reduced to exclude thermal effects (the exposure time length was adjusted to obtain the same total number of photons, e.g. 10 pulses per second for 10 seconds instead of 100 pulses for one second).

SUMMARY OF RESULTS FROM EXAMPLE II

| Laser Parameters | Total Energy (J/cm.$^2$) | No of Samples* | $Log_{10}$ Reduction** |
|---|---|---|---|
| 40 mJ/shot/cm.$^2$ 100 Hz, 1 sec | 4 | 36 | >5.2 |
| 40 mJ/shot/cm.$^2$ 30 Hz, 1 sec | 1.2 | 1 | >5.2 |
| 6 mJ/shot/cm.$^2$ 100 Hz, 1 sec | 0.6 | 3 | 2.7 |

-continued

SUMMARY OF RESULTS FROM EXAMPLE II

| Laser Parameters | Total Energy (J/cm.$^2$) | No of Samples* | $Log_{10}$ Reduction** |
|---|---|---|---|
| 40 mJ/shot/cm.$^2$ 2 Hz, 5 sec | 0.4 | 2 | <1.0 |
| 40 mJ/shot/cm.$^2$ 3 Hz, 1 sec | 0.12 | 2 | 3.3 |
| 6 mJ/shot/cm.$^2$ 2 Hz, 5 sec | 0.06 | 3 | 1.8 |

*Each sample had $1.5\times10^5$ spores on the surface of the 1 cm$^2$ target
**Defined as $\log_{10}$ ($1.5\times10^5$/number surviving)

The use of an energy density of 55 mJ/shot/cm$^2$ for more than 2 seconds resulted in physical damage of the strips (bubbling and browning effect).

The experimental results demonstrate that the killing efficiency of laser UV is dependent on the laser parameters employed and the number of bacterial organisms present, but it is independent of the substrate material. Most of the laser parameters tested revealed a high killing efficiency of bacterial numbers below $10^6$ cfu. The illumination period of one second at 40 mJ/shot/cm$^2$, 100 Hz, achieved a 100% kill of a bacterial concentration of $1.5\times10^5$ cfu. The high killing efficiency of $1.5\times10^5$ cfu at illumination times of one second and relatively low energy of repetition rate parameters such as 6 mJ/shot/cm$^2$ at 100 Hz and 40 mJ/shot/cm$^2$ at 3 Hz is of particular importance for carton sterilisation.

Figure 2:
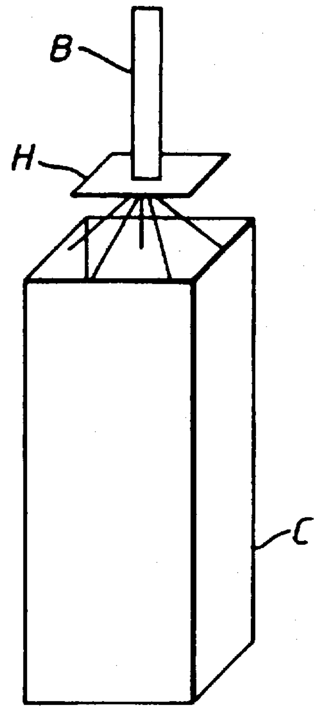
FIGS. 2 and 3 show diagrammatically two alternative systems usable in obtaining substantially uniform distribution of laser UV energy over the inside surface of an open-topped carton.
Figure 3:
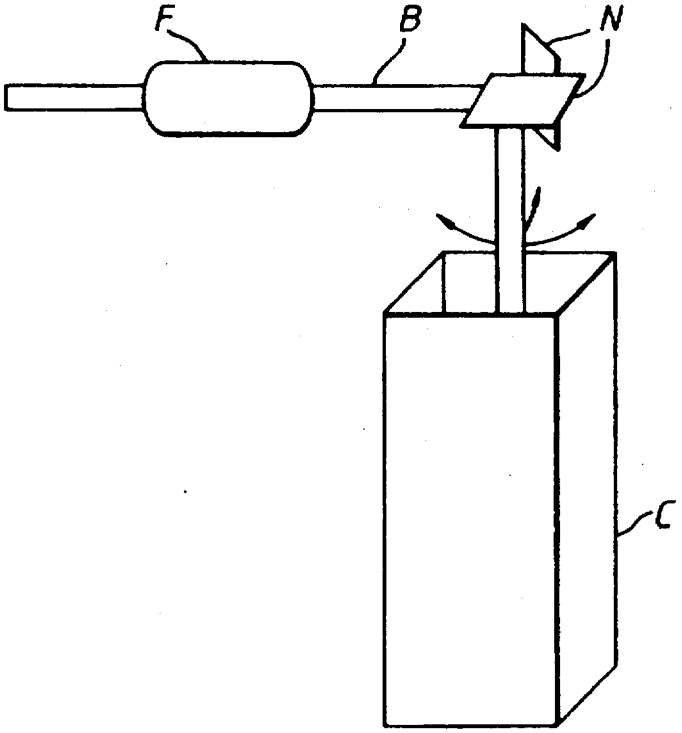

In order to obtain uniform energy distribution over the internal surface of the carton, the two systems illustrated in FIGS. 2 and 3 offer possible alternative solutions which can provide tailored energy distributions.

The first, illustrated in FIG. 2, utilises a computer-generated hologram H which diffracts the UV light beam B in a well-defined pattern. It consists of a complex surface structure or grating which is formed into the surface of a piece of glass. The design thereof requires computing facilities which can predict how light will interact with the grating structure. The grating is produced by coating the glass with a photoresist and writing the pattern into the photoresist with an electron beam. Developing the photoresist removes areas that have been exposed. The glass is then etched to reproduce the pattern that was present in the photoresist into the glass.

The second system, illustrated in FIG. 3, uses two galvanometers (not shown) to drive respective mirrors N that can be rotated about respective axes, thereby deviating the incident laser beam B. The combination of two scanners allows the beam to be directed in two axes. The addition of a third galvanometer (not shown) driving a linear translation stage, in other words a focus motion F, can be used to vary the separation of two lenses thereby changing the divergence of the beam.

It should be noted that the two systems have a fundamental difference. The hologram H addresses every point of the container C simultaneously whereas the galvanometer drive addresses areas sequentially.

Moreover, the hologram system has substantially no moving parts.

Example III

This Example described scanning of the whole carton, particularly the methods and microbiological tests used in the investigation of the effectiveness and efficiency of the UV laser irradiation over a range of laser energies and bacterial concentrations.

The basic test principle involved the spraying of empty, open-topped, gable-topped "ELOPAK" (Registered Trade Mark) cartons with a particular indicator organism, the irradiation of the cartons with laser energy and the investigation into the number or surviving bacterial cells after irradiation.

The indicator organism used for the tests was *Bacillus subtilis var. globigii.* To ensure a sufficient supply of the stock spore solution, 0.5 ml of the sample was subcultured into nutrient broth and allowed to grow at 37° C. for 48 hrs before centrifugation and harvesting into sterile Ringers solution. This solution was left at 4° C. for a minimum of seven days before being used in experiments.

The five inner surfaces of the carton were sprayed with the indicator organism. The spraying device used was a hand-held atomising gun that delivered the cells evenly over the carton surfaces. The range of bacterial concentrations was of the order of $10^7$ and $10^8$ cells per carton. The sprayed cartons were left to dry at room temperature in a laminar air hood for a maximum of 18 hrs before use.

To detect the surviving bacteria, a rinse test was used.

The spore suspension was diluted in Ringers solution to provide a dilution series from $10^{-1}$ up to $10^{-8}$ of the stock. 100 µl of each dilution was pipetted onto nutrient agar plates, streaked out, the plate inverted and incubated at 37° C. for 24 hrs before visual inspection of bacterial growth was carried out. 2 ml each of the appropriate bacterial dilution was sprayed into the test cartons and left to dry as described above. All reagent containers and petri-dishes were sterile before use and handled aseptically under LAF (Laminar Air Flow) conditions. The Ringers solution was autoclaved before the addition of Tween 20.

Spraying patterns and loading of the number of cells per carton were investigated by trial runs with water and the opening of the carton sides and confirmed by bacterial spraying and overlaying of agar as well as the recovery tests. The spray gun was cleaned with 70% ethanol prior to use and allowed to dry under LAF conditions. The carton lids were prepared by soaking in 70% ethanol, followed by a short 100% ethanol coverage and subsequent drying. A few sample lids were tested with nutrient broth for sterility after the ethanol treatment.

Each rinse test experiment included controls for untreated, ie. not laser-irradiated, cartons and cartons not sprayed with bacterial spores. The latter served as a control for background contamination. Most experiments included the testing of at least two bacterial dilutions. A typical experimental run would look as follows:

3 cartons sprayed with $10^{-1}$ dilution of the spore suspension; 3 further cartons sprayed with $10^{-2}$ dilution of the spore suspension.

For the $10^{-1}$ dilution; cartons 1, 2 and 3 were used for the rinse test, with 1 and 2 being the test and 3 the control, ie the carton was not laser-irradiated.

The same pattern was followed for the cartons sprayed with the $10^{-2}$ dilution of the spore suspension.

The cartons were placed (one at a time) in a special carton holder of the laser unit. After the irradiation time, the carton was removed from the holder and covered with a sterilised lid and the carton transported into the LAF. The handling of the carton in non-sterile environments was kept at an absolute minimum, but did involve some potential risk of contamination at the moment of carton removal from the carton holder and subsequent handling of the carton.

10 ml of the rinse test solution was pipetted into each rinse test carton. A sterilised lid was placed onto each carton and the cartons shaken vigorously for at least 30 times per side, then allowed to stand for a short time after which the volumes were poured into separate sterile universal containers. A dilution series was prepared from the recovered volume, using sterile Ringers solution. 250 µl or 500 µl volumes of each dilution and the neat recovery volume were streaked onto nutrient agar plates and incubated at 37° C. for 24 hrs.

The range of energies tested varied from 1.0 Joule to 4.0 Joule per $cm^2$ with irradiation times for approximately 10 minutes (this time period, which is sixty times a maximum commercially reasonable time of ten seconds per carton was chosen for practical experimental reasons to give a total dosage equal to the commercially desirable dosage applied over ten seconds). Each carton was placed into the holder at exactly the same position with the code print of the carton at the back of the holder. The top of the carton was attempted to be totally open, but was in some cases slightly bent. The irradiation procedure was automated and computer controlled.

Initial tests for the investigation of the test methods showed that spraying patterns resulted in an even distribution of bacteria and that recovery tests were in most experiments at the same concentration level as the original input. Below is a description of typical examples of the individual testing methods followed by a summary of the most significant experimental results.

A dilution series of the spore stock solution was prepared for each experimental run in order to assess the correct bacterial loading concentration per test sample.

The results from the dilution series were used to quantify the bacterial concentration sprayed into the cartons and to ascertain the recovery test accuracy. A control recovery test was included in each experimental run and the percentage recovery was calculated for each bacterial concentration. Once the recovery method was established to be reliable then the effectiveness of the laser irradiation could be measured against the recorded recovery result and the actual number of colonies recovered in the test sample were compared to expected numbers at that particular bacterial concentration. Typical recovery results were slightly below the expected result.

Rinse Test Example

| tests | rinse test sample $10^{-1}$ | rinse control sample $10^{-1}$ | dilution series |
|---|---|---|---|
| neat | >200 | lawn | lawn |
| $10^{-1}$ | 50 | lawn | lawn |
| $10^{-2}$ | 4 | uncountable | lawn |
| $10^{-3}$ | 1 | 278 | 1315 |
| $10^{-4}$ | 0 | 27 | 220 |

Calculation Example

The concentration of the stock was calculated from the dilution series result:

220 colonies at a dilution of $10^{-4}$ from a 100 µl sample of the plate, thus $2.2\times10^8$ stock.

The $10^{-1}$ dilution of the stock thus should be $2.2\times10^7$, but since 2 ml were used, the loading concentration of the carton was $4.4\times10^7$. The recovery in 20 ml of Ringers/Tween 20 solution and the 100 µl plate aliquot means that any result from the rinse test dilution needs to be multiplied by these factors. The control sample showed 278 colonies at $10^{-3}$ dilution of the recovered volume, thus the recovered concentration calculates to $278\times10^3\times10\times20=5.6\times10^7$. This differs from the loading concentration by $1.2\times10^7$ which is an insignificant difference, so to indicate no substantial problem with the recovery method. The actual laser-irradiated test sample gave approximately 200 colonies from the 100 μl aliquot of the 20 ml neat recovery volume, thus indicating that $4.0\times10^4$ colonies survived in this particular sample, giving a log reduction of <3.04 ie. log ($4.4\times10^7$:$4.0\times10^4$).

For the 250 μl sampling of the 10 ml rinse test volume the calculation factor is ×40 (ie. ×4×10), for the 500 μl sample of the 10 ml rinse test volume the calculation factor is ×20 (ie. ×2×10).

The definition of the Log reduction is as follows:

$\log_{10}$ (cells per carton: number of cells surviving per carton).

(III.3.5) Experimental Data

Cartons sprayed with $10^7$–$10^8$ cells were exposed to 1, 2, or 4 Joules/cm.$^2$ UV radiation and surviving spores determined by the rinse test applying 10 ml. rinse solution and taking 500 μl or 250 μl samples for plating. The kill rates found are given in the following Table.

Summary of results
10 ml rinse test volume/500 μl or 250 μl samples

| Loading cells/carton | Rinse Test recovered cells | Calculated cells per 10 ml | Energy J/cm$^2$ | $Log_{10}$ reduction |
|---|---|---|---|---|
| $2.4 \times 10^7$ | $80^{*1}$ | $1.6 \times 10^3$ | 1 | 4.18 |
| $2.4 \times 10^7$ | $2.4 \times 10^{3*1}$ | $4.8 \times 10^4$ | 1 | 2.7 |
| $2.4 \times 10^8$ | $2.2 \times 10^{4*1}$ | $4.4 \times 10^5$ | 1 | 2.7 |
| $1.3 \times 10^8$ | $8.6 \times 10^{3*2}$ | $3.4 \times 10^5$ | 1 | 2.58 |
| $1.3 \times 10^8$ | $8.8 \times 10^{3*2}$ | $3.5 \times 10^5$ | 1 | 2.57 |
| $1.3 \times 10^7$ | $1.12 \times 10^{2*2}$ | $4.48 \times 10^3$ | 1 | 3.46 |
| $2.6 \times 10^8$ | $65^{*2}$ | $2.6 \times 10^3$ | 2 | 5.0 |
| $2.6 \times 10^8$ | $1.44 \times 10^{2*2}$ | $5.76 \times 10^3$ | 2 | 4.7 |
| $2.6 \times 10^8$ | $85^{*2}$ | $3.4 \times 10^3$ | 2 | 4.9 |
| $2.6 \times 10^8$ | $27^{*2}$ | $1.08 \times 10^3$ | 4 | 5.38 |
| $2.6 \times 10^8$ | $27.5^{*2}$ | $1.10 \times 10^3$ | 4 | 5.37 |

$^{*1}$(500 μl)
$^{*2}$(250 μl)

The 2 Joule/cm$^2$ irradiation resulted in a 5 log reduction of micro-organisms and the even higher dosage of 4 Joule/cm$^2$ in a greater than 5 log reduction. The following can be concluded in summary from the experimental results:

Laser UV scanning of whole cartons can result in sterilisation of the cartons

2 Joule/cm$^2$ gives a 5 log reduction of *Bacillus subtilis var. globigii*

The carton internal area of 750 cm$^2$ requires 1500 joules of energy to be sterilised With an UV laser of a power of 150 W, it would take 10 seconds to achieve a 5 log reduction There is the possibility of using very low $H_2O_2$ concentrations in combination with the laser irradiation either to decrease the energy level required for the same time per carton or to decrease the time per carton for the same energy level.

Example IV

The quantitative assessment of kill rate when a combination of UV-laser and IR-laser is used simultaneously was investigated in this example.

The experimental set-up was designed so as to have additional information on the heat developed during exposure and also the effect of each of the treatments separately.

Blank carton material (Al-foil laminate) was used. The indicator organism was *Bacillus subtilis var. globigii*. A stock solution of spores from this strain was applied to the carton material.

The test involved three main phases, namely the coating of the bacteria onto pre-sterilized carton strips, the exposure of the strips to irradiation and the subsequent analysis of surviving spores on these strips.

The carton material was cut with a scalpel to give test strips of 2 cm×2 cm.

10-fold and 100-fold dilutions of the stock spore suspension (containing $4.5\times10^7$ cfu ml) were made in sterile saline (0.85% NaCl containing 0.02% Tween 20 to facilitate spreading).

These dilutions contained $4.5\times10^6$ and $4.5\times10^5$ cfu/ml, respectively.

Aliquots of 100 μl of each of the diluted suspensions were spread across strips to give a strip loading of $4.5\times10^5$ and $4.5\times10^4$ respectively.

Strips were left to dry overnight at room temperature. Some strips were left uncoated to check for sterility. After drying, each strip was placed in a sterile plastics universal bottle.

During irradiation the strips were held vertically on a presterilized 'bull dog' metal clip.

(IV. 2.2) Laser Calibration

The infra-red laser used for these tests was a 15 W $CO_2$ laser. This was controlled from a unit which allowed pulses of radiation of up to 6.6 seconds, and output power variable over the range 0–80% of the full output power.

The system was calibrated by measuring the temperature rise of a test piece of carton material of the same size as used for the biological tests. The temperature was measured using a thermocouple which was attached to the front surface of the card.

The IR does given was two 6.6 second pulses of 80% power (approximately 40 J/cm$^2$).

The maximum surface termperature that could be reached with front illumination was about 40° C. This was caused by the presence of a thin aluminium foil behind a polyethelene coating on this side of the card, which reflected a significant proportion of the IR radiation, preventing its absorption in the bulk of the card.

The excimer laser used a Krypton Fluorine gas mixture, and emitted at a wavelength of 248 nm. The laser pulse energy was about 300 mJ. The excimer radiation incident on the sample was calibrated using a detector placed behind a 2 cm×2 cm aperture. The pulse energy in this aperture was 125 mJ. In this way it was determined that an energy density of 1 J/cm$^2$ required 32 pulses.

Laser Irradiation Treatments

1. UV 1.0 Jcm$^{-2}$ only
2. IR to front of card
3. UV 1.0 Jcm$^{-2}$ and IR (front) simultaneously
4. UV 1.0 Jcm$^{-2}$ followed by IR (front) a few (2 to 3) seconds later
5. IR (front) followed by UV 1.0 Jcm$^{-2}$ many (30 ) seconds later.

Controls Cards coated with bacteria were left unirradiated to determine maximum recovery. Cards uncoated with bacteria were exposed to the atmosphere for about 30 sec to check for accidental contamination.

(IV. 2.6) Determination of Surviving Bacteria

After irradiation, the cards were immediately returned to their bottles and stored overnight at 4° C.

10 ml of sterile saline containing 0.1% Tween-20 was added to each bottle. The bottles were shaken vigorously for 30 seconds, after which the cards were removed and discarded. Duplicate samples of the washings (100 μl or 200 μl) were aseptically removed and spread on the surface of a nutrient agar plate. Some samples were serially diluted to facilitate counting. The plates were incubated at 37° C. for 24 hrs. and the colonies counted. From this, the total number of cfu in the 10 ml of washings was calculated, which gives the number of cfu recovered from the card.

The results are shown in the following Table.

TABLE

| | Treatment | Loaded cfu/ml | cfu Recovered | Log. Reduction | |
|---|---|---|---|---|---|
| 1 | (i) UV — only | $4.7 \times 10^5$ | $4.4 \times 10^3$ | 2.03 | ~1.98 |
| | (ii) | " | $5.6 \times 10^3$ | 1.92 | |
| 2 | (i) IR — only | " | $4.5 \times 10^5$ | 0.02 | ~0.02 |
| | (ii) | " | $4.5 \times 10^5$ | 0.02 | |
| 3 | (i) UV and IR, simultaneously | " | $2.4 \times 10^3$ | 2.29 | ~2.43 |
| | (ii) | " | $1.3 \times 10^3$ | 2.56 | |
| 4 | (i) UV-IR, sequential | " | $1.40 \times 10^3$ | 2.53 | ~2.43 |
| | (ii) | " | $2.2 \times 10^3$ | 2.33 | |
| 5 | (i) IR-UV, sequential | " | $7.2 \times 10^3$ | 1.81 | ~1.81 |
| | (ii) | " | contaminated | | |

A clear fact to emerge from the experiments was that IR treatment alone did not kill bacteria. It is also clear that all treatments involving IR and UV at 1.0 $Jcm^{-2}$ substantially simultaneously (Nos. 3 and 4) gave greater $\log_{10}$ reductions that UV alone, IR alone, or the sum of UV alone and IR alone. We therefore conclude that a synergistic effect occurs when IR and UV are applied substantially simultaneously.

We claim:

1. A method of sterilizing a solid surface, comprising providing a continuous solid surface, and irradiating said surface with laser UV of a wavelength which is bactericidal and producing a power density of laser UV at said surface such that the laser UV does not deleteriously melt said solid surface and yet renders micro-organisms thereat non-viable.

2. A method according to claim 1, wherein said surface is three-dimensional and the direction and intensity of the UV radiation is controlled to promote a substantially even intensity over said surface.

3. A method according to claim 2, wherein the UV radiation is applied by way of a hologram (H) in order to promote said substantially even intensity over said surface.

4. A method according to claim 1 and further comprising irradiating said surface with IR.

5. A method according to claim 4, wherein said IR is laser IR.

6. A method according to claim 4, wherein said surface is irradiated with said UV and said IR simultaneously.

7. A method according to claim 4, 5, or 6, wherein a synergistic effect is obtained between said UV and said IR in rendering micro-organisms at said surface non-viable.

8. A method according to claim 1, wherein hydrogen peroxide is present at said surface and is irradiated by said UV.

9. A method according to claim 8, wherein said hydrogen peroxide is present at said surface and a synergistic effect is obtained between said UV and said hydrogen peroxide in rendering micro-organisms at said surface non-viable.

10. A method of subjecting a continuous surface of a three-dimensional object to laser radiation which is at least partly laser UV, comprising providing a three-dimensional object having an extensive three-dimensional surface, and controlling the direction and intensity of the laser radiation, which is at least partly laser UV so as to promote a substantially even radiation intensity over said surface.

11. A method according to claim 10, wherein said radiation is applied by way of a hologram (H) in order to promote said substantially even intensity over said surface.

12. A method according to claim 10, wherein said surface is a food-contact surface of packaging material.

13. A method according to claim 12, wherein said food-contact surface is of thermoplastics.

14. A method according to claim 13, wherein said food-contact surface is of a thin polymer layer.

15. A method of sterilizing a material comprising providing a material to be sterilized, irradiating the material with IR and with laser UV simultaneously, to produce at said material a bactericidal effect rendering microorganisms at said material non-viable.

16. A method as claimed in claim 15, wherein said IR is laser IR.

17. A method as claimed in claim 15 or 16, wherein a synergistic effect is obtained between said UV and said IR in rendering micro-organisms at said material non-viable.

18. A method according to claim 15, wherein said material is a packaging material.

19. A method according to claim 18, wherein said material is thermoplastics.

20. A method according to claim 19, wherein said material is a thin polymer layer.

21. A method of sterilizing a material, comprising providing a material to be sterilized, irradiating the (same) material with IR and UV to produce at said material a bactericidal effect, characterized in that said UV is laser UV.

22. A method according to claim 21, wherein said IR is laser IR.

23. A method according to claim 21, wherein said material is irradiated with said IV and said IR simultaneously.

24. A method according to claim 21, 22, or 23, wherein a synergistic effect is obtained between said UV and said IR in rendering micro-organisms at said material non-viable.

25. A method according to claim 21, wherein said material is a packaging material.

26. A method according to claim 25, wherein said material is thermoplastics.

27. A method according to claim 26, wherein said material is a thin polymer layer.

28. A method of sterilizing a material, comprising providing a material to be sterilized, irradiating the (same) material with UV and exposing the same to hydrogen peroxide to produce at said material a bactericidal effect, characterized in that said UV is laser UV.

29. A method according to claim 28, wherein a synergistic effect is obtained between said laser UV and said hydrogen peroxide in rendering micro-organisms present at said material non-viable.

30. A method according to claim 28, wherein said material is a packaging material.

31. A method according to claim 30, wherein said material is thermoplastics.

32. A method according to claim 31, wherein said material is a thin polymer layer.

33. A method of sterilizing a solid surface constituting a food contact surface of packaging material, comprising providing a solid surface to be sterilized, irradiating said surface with laser UV of a wavelength which is bactericidal, thereby to render micro-organisms at said surface non-viable.

34. A method according to claim 33, wherein said surface is three-dimensional and the direction and intensity of the UV radiation is controlled to promote a substantially even intensity over said surface.

35. A method according to claim 34, wherein the UV radiation is applied by way of a hologram (H) in order to promote said substantially even intensity over said surface.

36. A method according to claim 33, and further comprising irradiating said surface with IR.

37. A method according to claim 36, wherein said IR is laser IR.

38. A method according to claim 36, wherein said surface is irradiated with said UV and said IR simultaneously.

39. A method according to claim 36, 37, or 38, wherein a synergistic effect is obtained between said IV and said IR in rendering micro-organisms at said surface non-viable.

40. A method according to claim 33, wherein hydrogen peroxide is present at said surface and is irradiated by said UV.

41. A method according to claim 40, wherein said hydrogen peroxide is present at said surface and a synergistic effect is obtained between said UV and said hydrogen peroxide in rendering micro organisms at said surface non-viable.

42. A method according to claim 33, wherein said food-contact surface is of thermoplastics.

43. A method according to claim 42, wherein said food-contact surface is of a thin polymer layer.

* * * * *